United States Patent [19]
Komaki et al.

[11] Patent Number: 5,695,974
[45] Date of Patent: Dec. 9, 1997

[54] PROCESS FOR PRODUCTION OF CARANE-3,4-DIOL

[75] Inventors: Ryohei Komaki, Toyonaka; Satoshi Mitsuda, Takarazuka; Keisuke Watanabe, Ashiya, all of Japan

[73] Assignee: Sumitomo Chemical Company, Limited, Osaka, Japan

[21] Appl. No.: 683,974

[22] Filed: Jul. 22, 1996

[30] Foreign Application Priority Data

Jul. 24, 1995 [JP] Japan ................................. 7-187056

[51] Int. Cl.$^6$ ......................................................... C12P 7/02
[52] U.S. Cl. ............................ 435/155; 435/170; 435/913
[58] Field of Search .................................. 435/155, 170, 435/913

[56] References Cited

PUBLICATIONS

L. Wackett et al., *Biochem. J.*, vol. 205, pp. 117–122 (1982).
J. Sutherland et al., *Applied Environmental Microbiology*, vol. 57, No. 11, pp. 3310–3316 (1991).

*Primary Examiner*—Herbert J. Lilling
*Attorney, Agent, or Firm*—Birch, Stewart, Kolasch & Birch, LLP

[57] ABSTRACT

There is provided a process for production of carane-3,4-diol which includes contacting a culture of filamentous fungus having an ability to produce carane-3,4-diol from 3-carene or 3,4-epoxycarane, cells collected from the culture or treated cells with 3-carene or 3,4-epoxycarane, then recovering the resulting carane-3,4-diol.

7 Claims, No Drawings

PROCESS FOR PRODUCTION OF CARANE-3,4-DIOL

FIELD OF THE INVENTION

The present invention relates to a process for production of carane-3,4-diol.

DESCRIPTION OF RELATED ART

Carane-3,4-diol is a compound having good repellent effects on hematophagous vermin such as mosquito, gnat, stable fly, sand fly and biting midge, and sanitary vermin such as housefly (JP-A 5-4901).

As a process for production of carane-3,4-diol, there has been hitherto known a chemical process using, as a raw material, natural 3-carene or 3,4-epoxycarane.

However, the prior art process has a problem in that the process requires facilities of high costs because of severe reaction conditions such as high temperature and high pressure as well as complicated procedures such as post-treatment and the like.

Therefore, a main object of the present invention is to provide a process for production of carane-3,4-diol using mild reaction conditions and without the necessity of having to use complicated procedures.

Under the above circumstances, the present inventors have found that certain filamentous fungi have an ability to produce carane-3,4-diol from 3-carene or 3,4-epoxycarane.

SUMMARY OF THE INVENTION

The present invention provides a process for production of carane-3,4-diol which comprises contacting a culture of filamentous fungi having an ability to produce carane-3,4-diol from 3-carene or 3,4-epoxycarane, cells collected from the culture or treated cells with 3-carene or 3,4-epoxycarane, and then recovering the resulting carane-3,4-diol (hereinafter, referred to as "the present process").

According to the present invention carane-3,4-diol can be produced from 3-carene or 3,4-epoxycarane at room temperature and atmospheric pressure without having to use complicated procedures.

DETAILED DESCRIPTION OF THE PREFERRED EMBODIMENT

The present invention is described in detail below.

Filamentous fungi to be used in the present invention are not specifically limited, but any strain of filamentous fungi that may have an ability to produce carane-3,4-diol from 3-carene or 3,4-epoxycarane, for example, a wild strain, mutant strain or recombinant strain resulting from cell fusion or genetic manipulation, can be used. Such an ability has not been known for any microorganism.

The filamentous fungi having the ability to produce carane-3,4-diol from 3-carene or 3,4-epoxycarane can be isolated by screening from natural sources such as soil, vegetable manure heaps, or river water and using a medium that is typically employed for culturing filamentous fungi, for example, Saburo-Dextrose Medium (Difco). Examples of filamentous fungi used for the present invention arc filamentous fungi belonging to the genus Phaenerochaete and Cunninghamella (see, for example, Kinruizukan, First Vol., pp. 282-283, published by Kodansha, (1978); Appl. Environ. Microbiol., 57, 3310(1991); Biochem. J., 205, 117(1982)). An example of filamentous fungi belonging to genus Phaenerochaete is *Phaenerochaete chrysosporium* IFO 31249 (Proc. Natl. Acad. Sci., (1975), 72, 2515). An example of filamentous fungi belonging to genus Cunninghamella is *Cunninghamella echinulata var elegans*, ATCC 9245 (J. Am. Chem. Soc. (1965), 77, 5767). Among the above filamentous fungi, the former having the IFO number is described in List of Cultures, 9th edition, 1992, published by the Institute For Fermentation, Osaka (IFO) and is available from that laboratory. The latter having ATCC number is described in Catalogue of Filamentous Fungi, 18th edition, 1991 published, by the American Type Culture Collection (ATCC) and is available from ATCC.

Examples of the medium to be used for culturing filamentous fungi include, for example, Saburo-Dextrose Medium (Difco). Examples of carbon sources are those which are utilized by filamentous fungi, for example, sugars such as glucose, fructose, sucrose and dextrin, sugar alcohols such as glycerol and sorbitol, and organic acids such as fumaric acid and citric acid. An amount of the carbon sources to be added to the medium is preferably about 0.1% (w/v) to about 10% (w/v). Examples of nitrogen sources are those which can be utilized by filamentous fungi, for example, ammonium salts of inorganic acids such as ammonium chloride and ammonium phosphate, ammonium salts of organic acids such as ammonium fumarate and ammonium citrate, and natural nitrogen sources such as broth extract, peptone, yeast extract, corn steep liquor, and casein hydrolysate. Among these materials many of the organic nitrogen sources can also be used as carbon sources. An amount of nitrogen sources to be added to the medium is preferably 0.1% (w/v) to about 10% (w/v). As the inorganic acid salt, an alkali metal phosphate such as potassium phosphate and sodium phosphate, alkali metal chloride such as potassium chloride and sodium chloride, or metal, sulfate such as magnesium sulfate and ferrous sulfate can be used. An amount of the inorganic salt to be added to the medium is preferably about 0.001% (w/v) to about 1% (w/v). The filamentous fungi are cultured at a temperature of about 15° C. to about 40° C., preferably about 24° C. to about 37° C., at a pH of about 5 to about 8, preferably about 5 to about 7 for a time of 12 hours to 5 days under aerobic conditions. Cells collected from the filamentous culture thus obtained can be appropriately used as nitrogen sources. Further, treated cells such as lyophilized cells, acetone-dried cells, fractured cells obtained by fracturing at a low temperature (Biochem. J., (1982) 205, 117), self-digested cells, ultrasonic-treated cells, and extracted cells may be used as nitrogen sources. Further, enzymes themselves obtained by purification by means of a combination of the known methods from the above cells or treated cells may be used as the nitrogen sources. Alternatively, immobilized treated cells obtained by immobilizing the above cells or treated cells using a known method such as the polyacrylamide gel method, sulfur-containing polysaccharide gel method (carrageenan gel method), alginate gel method and agar method may also be used.

The reaction is usually conducted by contacting the culture, cells collected from the culture, or the treated cells with 3-carene or 3,4-epoxycarane as a substrate. The substrate may be added to the culture, or The cells collected from the culture or the treated cells may be added to an aqueous solution of the substrate. The concentration of the substrate is usually about 0.01% (w/v) to about 5% (w/v), preferably about 0.05% (w/v) to about 1% (w/v). A higher alcohol or a surfactant such as a polyether may be added to the reaction to improve the contact between the substrate and the culture, the cells collected from the culture or the treated cells. The concentration of the surfactant is usually about 0.0001% (w/v) to about 0.001% (w/v). The pH in the reaction is usually about 5 to about 8. The reaction temperature is usually about 10° C. to about 40° C., preferably about 25° C. to about 40° C. The reaction time depends upon the concentration of the cells (or the enzyme concentration) and is usually 2 to 4 days when the reaction is carried out at a substrate concentration of 0.5% (w/v) at a reaction temperature of 30° C. using the normal culture.

The 3-carene to be used includes (+) −1S, 6R-3-carene and (−) −1R, 6S-3-carene. 3,4-Epoxycarane to be used in the present process can be obtained by epoxidation reaction of 3-carene with an epoxidizing agent or a conventional method.

The carane-3,4-diols produced by the present process are ususally trans diols. When (+) −1S, 6R-3-carene or its epoxide is used as a starting material, a carane-3,4-diol compound such as the 1S, 3R, 4R, 6R or 1S, 3S, 4S, 6R isomer can be obtained.

The produced carane-3,4-diol is usually recovered from the reaction mixture by a conventional separation method such as extraction and/or distillation, and may be further purified by a method such as column chromatography or the like, if necessary.

The following Examples illustrate the present invention in detail but are not to be construed to limit the scope thereof.

EXAMPLE 1

100 Ml of malt extract-glucose medium (pH 5.5) containing 2.0% (w/v) malt extract, 2.0% (w/v) glucose, 0.024% (w/v) maltose, 0.018% (w/v) yeast extract and 0.0005% (w/v) Tween 80 was placed in a 500 ml shaking flask, followed by sterilization at 120° C. for 20 minutes. The medium was inoculated with one loop of *Phaenerochaete chrysosporium* IFO 31249, followed by shaking for cultivation at 30 ° C. for 3 days. To the resultant culture was added 0.5 ml of (+) 3-carene, followed by further shaking for 4 days. After cultivation, the culture was filtered to remove the cells, and 36 g of sodium chloride was added to the filtrate for salting. To the supernatant after salting was added 200 ml of ethyl ether to extract the resultant carane-3,4-diol. The ether extract was concentrated to dryness, the residue was weighed, and the ingredients of the residue were subjected to GC-analysis to measure the quantity of carane-3, 4-diol.

(GC analysis conditions)

Column: HR-20M (manufactured by Shinwakako), 30 m

Column temperature: Temperature is raised from 100° C. to 160° C. at 5° C./min. and, thereafter, maintained constant.

Injector, detector temperature: 240° C.

As the result, 20 mg of the residue were found to contain 7.6 mg of 1S,3R,4R,6R-carane-3,4-diol and 0.3 mg of 1S,3S,4S,6R-carane-3,4-diol.

EXAMPLE 2

100 Ml of malt extract-glucose medium (pH 5.5) containing 2.0% (w/v) malt extract, 2.0% (w/v) glucose, 0.024% (w/v) maltose., 0.018% (w/v) yeast extract and 0.0005% (w/v) Tween 80 was placed in a 500 ml shaking flask, followed by sterilization at 120° C. for 20 minutes. The medium was inoculated with one loop of *Phaenerochaete chrysosporium* IFO 31249, followed by shaking to culture at 30° C. for 3 days. The cells was collected from the resultant culture by centrifugation (8000×g, 20 min., 5° C.), and the collected cells were suspended in 100 ml of a 0.1M sodium carbonate buffer (pH 5.5) containing 0.5 ml of 3,4-epoxycarane (a stereoisomer in which epoxy group and isopropylidene group of 3,4-epoxycarane take a trans orientation with respect to the cyclohexane ring). The suspension was placed in a 500 ml shaking flask, followed by reaction at 30° C. for 4 days. After the reaction mixture, the reaction was filtered to remove the cells, and 36 g of sodium chloride was added to the filtrate for salting. To the supernatant after salting was added 200 ml of ethyl ether to extract the resultant carane-3,4-diol. The ether extract was concentrated to dryness, the residue was weighed, and the ingredients of the residue were subjected to GC-analysis to measure the quantity of carane-3,4-diol.

(GC analysis conditions)

Column: HR-20M (manufactured by Shinwakako), 30 m

Column temperature: Temperature is raised from 100° C. to 160° C. at 5° C./min. and, thereafter, maintained constant.

Injector, detector temperature: 240° C.

As the result, 298 mg of the residue were found to contain 205 mg of 1S,3R,4R,6R-carane-3,4-diol and 15 mg of 1S,3S,4S,6R-carane-3,4-diol.

EXAMPLE 3

100 Ml of Saburo-Dextrose (manufactured by Difco) liquid medium (pH 5.2) was placed in a 500 ml shaking flask, followed by sterilization at 120° C. for 20 minutes. This medium was inoculated with one loop of *Cunninghamella echinulata var elegans*, ATCC 9245, followed by shaking at 30° C. for 3 days. To the resultant culture was added 0.5 ml of (+) 3-carene, and the shaking was continued for 4 days. After cultivation, the culture was filtered to remove the cells, 36 g of sodium chloride was added to the filtrate for salting. To the supernatant after salting was added 200 ml of ethyl ether to extract the produced carane-3,4-diol. The ether extract was concentrated to dryness, the residue was weighed, and the ingredients of the residue were subjected to GC-analysis to measure the quantity of carane-3, 4-diol.

(GC analysis conditions)

Column: HR-20M (manufactured by Shinwakako), 30 m

Column temperature: Temperature is raised from 100° C. to 160° C. at 5° C./min. and, thereafter, maintained constant.

Injector, detector temperature: 240° C.

As the result, 73 mg of the residue were found to contain 61 mg of 1S,3R,4R,6R-carane-3,4-diol and 2.2 mg of 1S,3S, 4S,6R-carane-3,4-diol.

EXAMPLE 4

100 Ml of Saburo-Dextrose (manufactured by Difco) liquid medium (pH 5.2) was placed in a 500 ml shaking flask, followed by sterilization at 120° C. for 20 minutes. This medium was inoculated with one loop of *Cunninghamella echinulata var elegans*, ATCC 9245, followed by shaking at 30° C. for 3 days. The resultant culture was filtered to collect the cells, the collected cells were suspended in 50 ml of an ice-cooled phosphate buffer (pH 7.2, containing 20 mM, EDTA 1.5 mM, DTT 1 mM, glycerol 10%). The suspension was subjected to a blender for 10 minutes under cooling with liquid nitrogen. The fractured cells were centrifuged (12000 g, 15 min.) to recover the supernatant. The recovered supernatant was subjected to ultracentrifugation (100000×g, 1 hour, 5° C.) to obtain the enzyme pellet as the precipitate. The enzyme pellet was suspended in 100 ml of the same phosphate buffer, the suspension was placed in a 500 ml shaking flask, and 0.5 ml of 3,4-epoxycarane (a stereoisomer in which the epoxy group and isopropylidene group of 3,4-epoxycarane take a trans orientation with respect to the cyclohexane ring) was added thereto to react at 30° C. for 4 days. After the reaction, the reaction was filtered to remove the cells, and 36 g of sodium chloride was added to the filtrate for salting. 200 ml of ethyl ether was added to the supernatant after salting to extract the produced carane-3,4-diol. The ether extract was concentrated to dryness, the residue was weighed, and the ingredients of the residue were subjected to GC-analysis to measure the quantity of carane-3,4-diol.

(GC analysis conditions)

Column: HR-20M (manufactured by Shinwakako), 30 m

Column temperature: Temperature is raised from 100° C. to 160° C. at 5° C./min. and, thereafter, maintained constant.

Injector, detector temperature: 240° C.

As the result, 247 mg of the residue were found to contain 146 mg of 1S,3R,4R,6R-carane-3,4-diol and 2 mg of 1S3S, 4S,6R-carane-3,4-diol.

What is claimed is:

1. A process for the production of carane-3,4-diol which comprises
    contacting a culture of filamentous fungus belonging to a genus selected from the group consisting of Phaenerochaete and Cunninghamella and having the ability to produce carane-3,4-diol from 3-carene or 3,4-epoxycarane, cells collected from said culture or treated cells thereof with 3-carene or 3,4-epoxycarane; and
    recovering the resulting carane-3,4-diol from the reaction mixture.

2. The process according to claim 1, wherein 3-carene is the (+) compound, and carane-3,4-diol is the 1S,3S,4S,6R-stereoisomer or the 1S,3R,4R,6R-stereoisomer.

3. The process according to claim 1, wherein 3,4-epoxycarane is an epoxide of (+) 3-carene, and carane-3,4-diol is the 1S,3S,4S,6R-stereoisomer or the 1S,3R,4R,6R-stereoisomer.

4. The process according to claim 1, wherein the filamentous fungus is *Phaenerochaete chrysosporium*.

5. The process according to claim 4, wherein the filamentous fungus is *Phaenerochaete chrysosporium* IFO 31249.

6. The process according to claim 1, wherein the filamentous fungus is *Cunninghamella echinulata*.

7. The process according to claim 6, wherein the filamentous fungus is *Cunninghamella echinulata var elegans* ATCC 9245.

* * * * *